United States Patent
Lee et al.

(10) Patent No.: US 7,791,730 B2
(45) Date of Patent: Sep. 7, 2010

(54) SURFACE PLASMON RESONANCE METER

(75) Inventors: Chih-Kung Lee, Taipei (TW);
Shu-Sheng Lee, Taipei (TW);
Chih-Hsiang Sung, Taipei (TW);
Yi-Hao Chen, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 12/422,891

(22) Filed: Apr. 13, 2009

(65) Prior Publication Data
US 2010/0053625 A1    Mar. 4, 2010

(30) Foreign Application Priority Data
Aug. 29, 2008    (TW) ............................... 97133180 A

(51) Int. Cl.
*G01N 21/55* (2006.01)
(52) U.S. Cl. ..................................... 356/445; 356/442
(58) Field of Classification Search .......... 356/442–446
See application file for complete search history.

(56) References Cited

U.S. PATENT DOCUMENTS

| | | | |
|---|---|---|---|
| 6,462,809 B1 * | 10/2002 | Ryan et al. | 356/136 |
| 2006/0227328 A1 * | 10/2006 | Vanwiggeren et al. | 356/445 |
| 2008/0042068 A1 * | 2/2008 | Nishinaga et al. | 250/370.01 |

* cited by examiner

Primary Examiner—Gregory J Toatley, Jr.
Assistant Examiner—Iyabo S Alli

(57) ABSTRACT

A surface plasmon resonance meter is provided, including a backlight module, a line-slot plate, a parabolic mirror, a linear polarizer, a sensing chip, a prism and a photo detector array. The line-slot plate includes a light outlet. A light beam travels in the backlight module, and leaves the backlight module through the light outlet. The position of the line-slot plate is matched on a predetermined focal point of the parabolic mirror. The light beam is reflected by the parabolic mirror to be a parallel light beam, and travels trough the linear polarizer to the prism. The prism includes a light entering surface, a detection surface and a light exiting surface. The light beam enters the prism through the light entering surface, contacts the sensing chip with total internal reflection, and finally leaves the prism through the light exiting surface to be received by the photo detector array.

13 Claims, 3 Drawing Sheets

SURFACE PLASMON RESONANCE METER

CROSS REFERENCE TO RELATED APPLICATIONS

This Application claims priority of Taiwan Patent Application No. 097133180, filed on Aug. 29, 2008, the entirety of which is incorporated by reference herein.

BACKGROUND OF THE INVENTION

1. Field of the Invention

The invention relates to a surface plasmon resonance meter, and more particularly to a surface plasmon resonance meter with smaller volume.

2. Description of the Related Art

Conventional surface plasmon resonance meters, for example, a surface plasmon resonance meter with intensity modulation detects a specimen by light beams of particular wavelengths and incident angles. The incident angle of the light beam nears a surface plasmon resonance angle. The brightness of a reflected light beam violently changed when the incident angle thereof nears the surface plasmon resonance angle. When the surface plasmon resonance angle is changed, the brightness of a reflected light beam is obviously changed, and the variation of refractive index can be detected therefrom.

However, conventional surface plasmon resonance meters with intensity modulation have low noise ratio and low resolution. Additionally, conventional surface plasmon resonance meters with intensity modulation utilize particular optical structures, optical elements and light sources, thus requiring a complicated alignment process and increased volume. Conventional surface plasmon resonance meter with intensity modulation is thus, difficult to operate and be carried.

BRIEF SUMMARY OF THE INVENTION

A detailed description is given in the following embodiments with reference to the accompanying drawings.

The embodiment provides a surface plasmon resonance meter, comprising a backlight module, a line-slot plate, a parabolic mirror, a linear polarizer, a sensing chip, a prism and a photo detector array. The backlight module comprises a light source, a light guide, a diffuser, a Brightness Enhancement Film and a reflector. The Brightness Enhancement Film is transparent optical film that increases brightness of backlight module through improved management of the existing light. For example, prism sheets with microreplicated prism structures could be a Brightness Enhancement Film, which increase the brightness of backlight by focusing the light toward the user.

The light source provides a light beam. The light beam enters the light guide from the light source. The line-slot plate comprises a light outlet, wherein the light beam travels from the light guide, passes the diffuser and the Brightness Enhancement Film to the line-slot plate, is reflected by the line-slot plate toward the reflector, is multi-reflected between the line-slot plate and the reflector, and leaves the backlight module through the light outlet. The light beam is reflected by the parabolic mirror to be shaped into a parallel light beam, and travels from the parabolic mirror to the linear polarizer. The prism comprises a light entering surface, a detection surface and a light exiting surface, wherein the light beam travels from the linear polarizer, enters the prism through the light entering surface, contacts the sensing chip at the detection surface, is totally reflected by the sensing chip, and leaves the prism through the light exiting surface. The photo detector array receives the light beam emitted from the light exiting surface.

Utilizing the embodiment of the invention, a small-sized light emitting diode is utilized as light source, and a backlight module is utilized to uniform the light beam. With the parallel light beam generated by the parabolic mirror and high manufacturing resolution, the size of the surface plasmon resonance meter of the invention is reduced. Additionally, sensitivity of the surface plasmon resonance meter can be further improved by utilizing a red light emitting diode and coating a gold film on a sensing chip. The surface plasmon resonance meter of the embodiments of the invention is easy to operate and be carried.

BRIEF DESCRIPTION OF THE DRAWINGS

The invention can be more fully understood by reading the subsequent detailed description and examples with references made to the accompanying drawings, wherein:

FIG. 3b is a sectional view along direction I-I of FIG. 3a.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
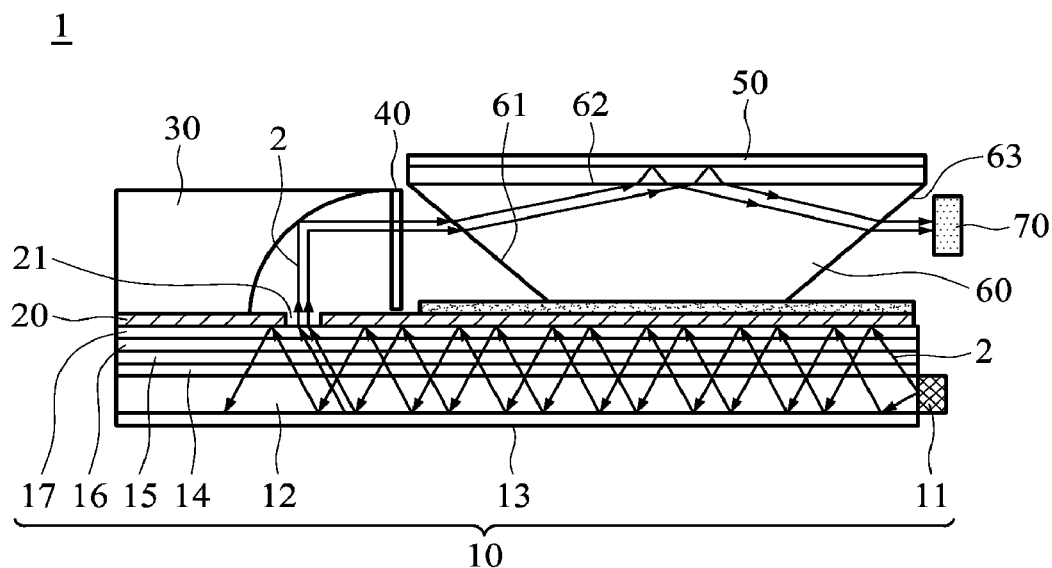
FIG. 1 shows a surface plasmon resonance meter of an embodiment of the invention.

FIG. 1 shows a surface plasmon resonance meter 1 of an embodiment of the invention, which is surface plasmon resonance meter with intensity modulation, comprising a backlight module 10, a line-slot plate 20, a parabolic mirror 30, a linear polarizer 40, a sensing chip 50, a prism 60 and a photo detector array 70. A light beam 2 is emitted from the backlight module 10, passes the line-slot plate 20, is reflected by the parabolic mirror 30, passes the linear polarizer 40, enters the prism 60 to contact the sensing chip 50, is reflected by the sensing chip 50, and leaves of the prism 60 to be received by the photo detector array 70.

The backlight module 10 comprises a light source 11, a light guide 12, a reflector 13, a diffuser 14, a vertical prism sheet 15, a horizontal prism sheet 16 and a protection film 17, where the vertical prism sheet 15 and the horizontal prism sheet 16 combined to form a Brightness Enhancement Film. The line-slot plate 20 is disposed above the protection film 17. The light guide 12, the diffuser 14, the vertical prism sheet 15, the horizontal prism sheet 16 and the protection film 17 are sandwiched between the line-slot plate 20 and the reflector 13. The backlight module 10 is an edge-light backlight module.

The line-slot plate 20 comprises a light outlet 21. The light outlet 21 is a longitudinal slot.

The light source 11 provides the light beam 2. The light beam 2 enters the light guide 12 through a side surface thereof, is multi-reflected between the line-slot plate 20 and the reflector 13, passes the light guide 12, the diffuser 14, the vertical prism sheet 15, the horizontal prism sheet 16 and the protection film 17, and leaves the backlight module 10 through the light outlet 21.

A particular distance is formed between the light outlet 21 and the light source 11. When the light beam 2 travels from the light source 11 to the light outlet 21, the light beam 2 is repeatedly reflected between the line-slot plate 20 and the reflector 13 to be uniformed. The light outlet 21 has a particular width, wherein after the light beam 2 passes the light outlet 21 and is reflected toward a horizontal direction, the light beam 2 has a cross-sectional area equal to the area of a light entering surface 61 of the prism 60.

The parabolic mirror 30 comprises a predetermined focal point, and the light outlet 21 is matched on the predetermined focal point. The light beam 2 is emitted from the light outlet 21 and is reflected by the parabolic mirror 30 to be a parallel light beam. Next, the light beam 2 passes the linear polarizer 40 to the prism 60.

The prism 60 comprises the light entering surface 61, a detection surface 62 and a light exiting surface 63, wherein the light beam 2 travels from the linear polarizer 40, enters the prism 60 through the light entering surface 61, contacts the sensing chip 50 at the detection surface 62, is total reflected by the sensing chip 50, and leaves the prism 60 through the light exiting surface 63 to the photo detector array 70.

Figure 2:
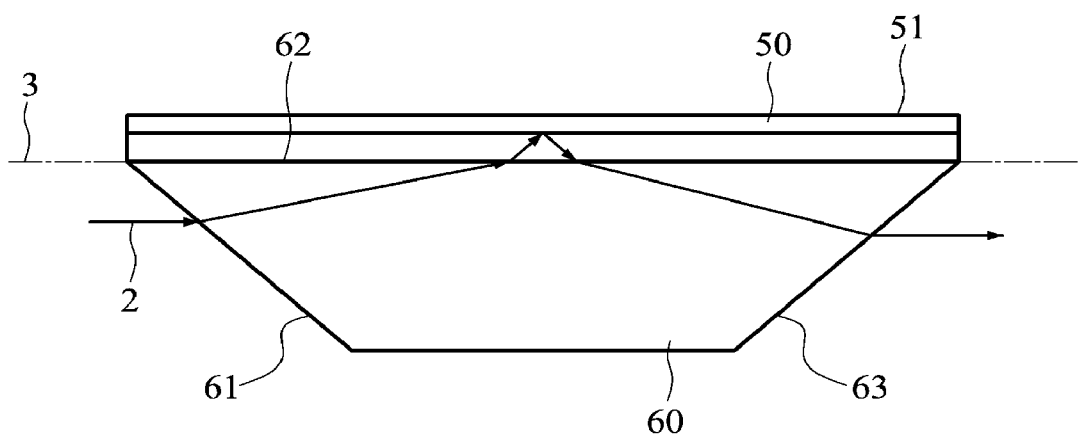
FIG. 2 shows a detailed structure of a prism of the embodiment of FIG. 1.

With reference to FIG. 2, in the embodiment of the invention, an incident angle is formed between the light beam 2 and a datum plane 3 when the light beam 2 enters the prism 60 through the light entering surface 61. In one embodiment of the invention, the incident angle is zero. The datum plane 3 is parallel to the detection surface 62.

The light source 11 is a light emitting diode, and preferably, a red light emitting diode. In one embodiment, the light source comprises a plurality of the light emitting diodes, and the light emitting diodes are series connected.

In one embodiment, the prism 60 is a trapezoid or a Dove prism.

In one embodiment, the sensing chip 50 further comprises a gold film 51. The gold film 51 is formed on a surface of the sensing chip 50, and contacts the specimen.

Utilizing the embodiment of the invention, a small-sized light emitting diode is utilized as a light source, and a backlight module is utilized to uniform a light beam. The size of the surface plasmon resonance meter is reduced when compared to conventional surface plasmon resonance meters. Additionally, sensitivity of the surface plasmon resonance meter is improved by utilizing a red light emitting diode and coating a gold film on the sensing chip.

Figure 3A:
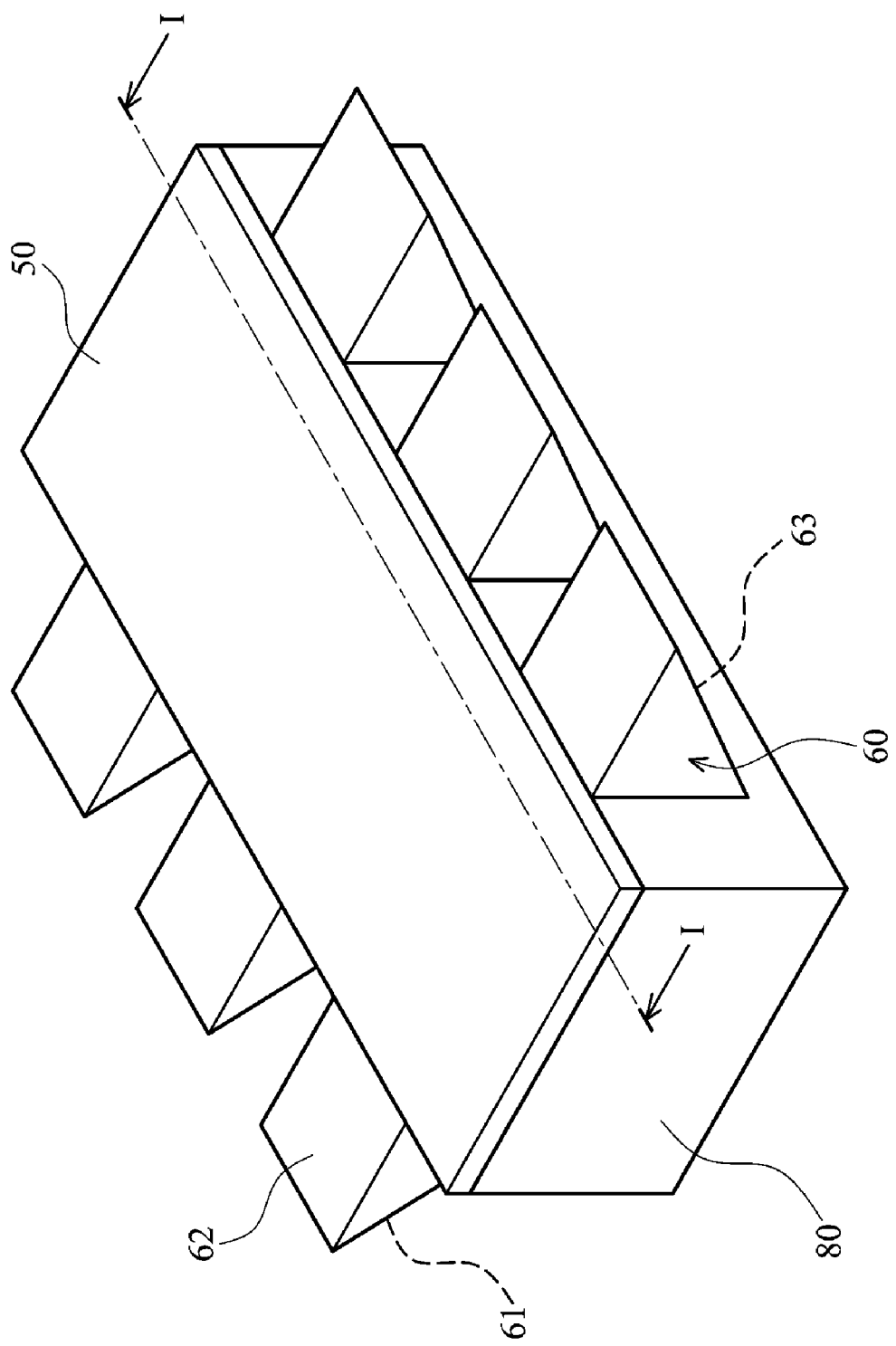
FIG. 3a shows a supporting base of the embodiment of FIG. 1.
Figure 3B:
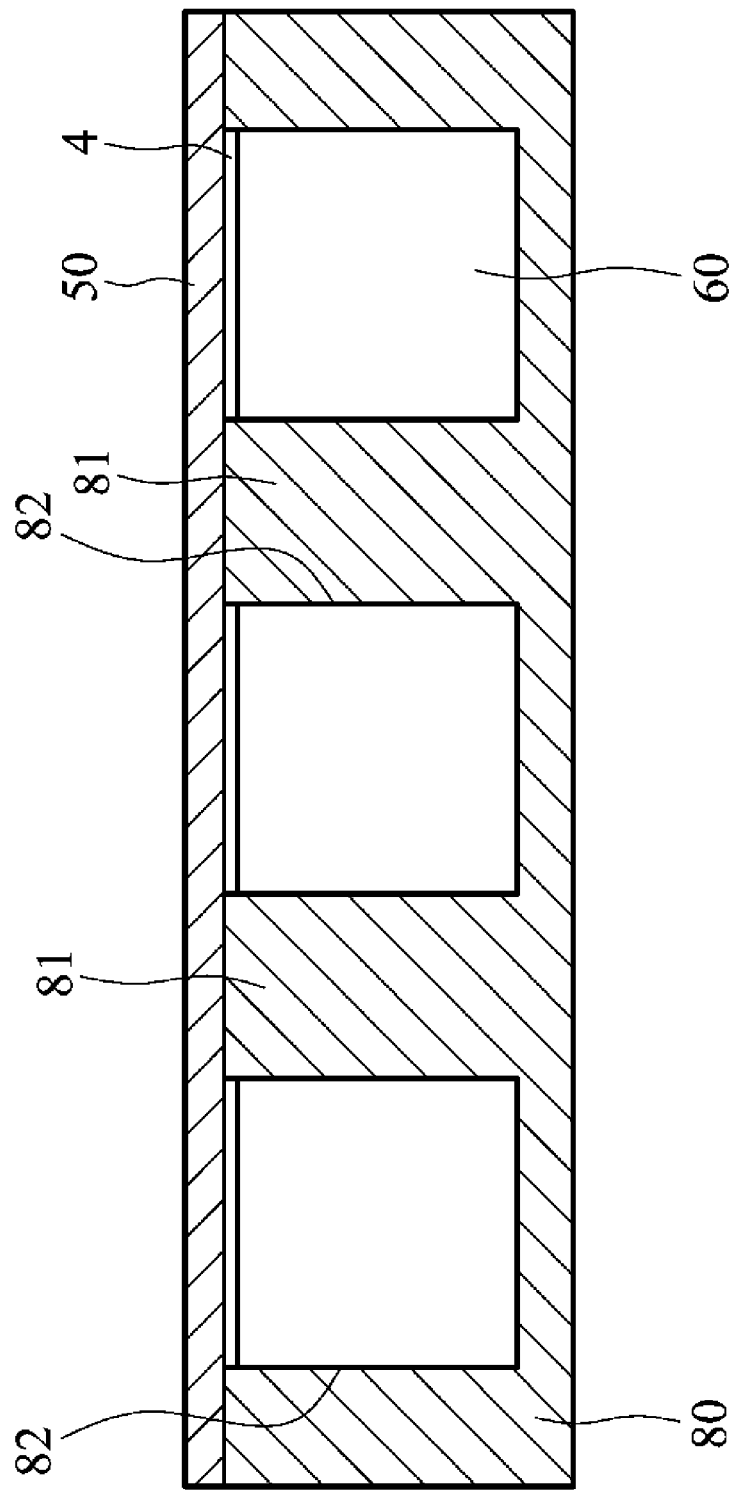

With reference to FIG. 3a, in one embodiment, the surface plasmon resonance meter 1 has a plurality of prisms 60 disposed in a supporting base 80. FIG. 3b is a sectional view along direction I-I of FIG. 3a, wherein the supporting base 80 comprises protrusions 81 and grooves 82. The grooves 82 are formed between the protrusions 81. The prisms 60 are disposed in the grooves 82. The sensing chip 50 is supported by the protrusions 81. Gaps are formed between the prisms 60 and the sensing chip 50. Coupling oil 4 is filled in the gap.

The supporting base of the embodiment supports the sensing chip, and prevents the sensing chip from deforming. As well, the supporting base controls the position of the coupling oil to uniform distribution thereof.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A surface plasmon resonance meter, comprising:
    a backlight module, comprising:
        a light source, providing a light beam;
        a light guide, wherein the light beam enters the light guide from the light source;
        a diffuser;
        a Brightness Enhancement Film; and
        a reflector;
    a line-slot plate, comprising a light outlet, wherein the light beam travels from the light guide, passes the diffuser and the Brightness Enhancement Film to the line-slot plate, is reflected by the line-slot plate toward the reflector, is multi-reflected between the line-slot plate and the reflector, and leaves the backlight module through the light outlet;
    a parabolic mirror, receiving the light beam from the light outlet, wherein the light beam is reflected by the parabolic mirror to be shaped into a parallel light beam;
    a linear polarizer, wherein the light beam travels from the parabolic mirror to the linear polarizer;
    a sensing chip;
    a prism, comprising a light entering surface, a detection surface and a light exiting surface, wherein the light beam travels from the linear polarizer, enters the prism through the light entering surface, contacts the sensing chip at the detection surface, is totally reflected by the sensing chip, and leaves the prism through the light exiting surface; and
    a photo detector array, receiving the light beam emitted from the light exiting surface.

2. The surface plasmon resonance meter as claimed in claim 1, wherein the light is emitted from the light source, and enters the light guide through a side surface thereof.

3. The surface plasmon resonance meter as claimed in claim 1, wherein the light source comprises a light emitting diode.

4. The surface plasmon resonance meter as claimed in claim 1, wherein the light source comprises a red light emitting diode.

5. The surface plasmon resonance meter as claimed in claim 1, wherein the light source comprises a plurality of light emitting diodes, and the light emitting diodes are series connected to each other.

6. The surface plasmon resonance meter as claimed in claim 1, wherein the light outlet is a slot.

7. The surface plasmon resonance meter as claimed in claim 1, wherein the parabolic mirror comprises a predetermined focal point.

8. The surface plasmon resonance meter as claimed in claim 7, wherein the light outlet is matched on the predetermined focal point.

9. The surface plasmon resonance meter as claimed in claim 1, wherein the surface plasmon resonance meter is a surface plasmon resonance meter with intensity modulation.

10. The surface plasmon resonance meter as claimed in claim 1, wherein sensing chip comprises a gold film, formed on a surface thereof.

11. The surface plasmon resonance meter as claimed in claim 10, wherein a thickness of the gold film is designed to provide improved sensitivity.

12. The surface plasmon resonance meter as claimed in claim 1, further comprising a supporting base, wherein the supporting base comprises a plurality of protrusions and a groove, the prism is disposed in the groove, the protrusions contact and support the sensing chip, and a gap is formed between the prism and the sensing chip.

13. The surface plasmon resonance meter as claimed in claim 12, further comprising a coupling oil disposed in the gap.

* * * * *